(12) United States Patent
Mittendorf et al.

(10) Patent No.: US 6,284,788 B1
(45) Date of Patent: *Sep. 4, 2001

(54) USE OF KNOWN AGONISTS OF THE CENTRAL CANNABINOID RECEPTOR CB1

(75) Inventors: Joachim Mittendorf, Wuppertal; Jürgen Dressel, Radevormwald; Michael Matzke, Wuppertal; Jürgen Franz, Haan; Peter Spreyer, Düsseldorf; Verena Vöhringer; Joachim Schuhmacher, both of Wuppertal; Arno Friedl, Bergisch Gladbach; Ervin Horvath, Leverkusen; Frank Mauler, Overath; Jean-Marie-Viktor De Vry, Rösrath; Reinhard Jork, Overath, all of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/024,590

(22) Filed: Feb. 17, 1998

(30) Foreign Application Priority Data

Feb. 21, 1997 (DE) ............................................. 197 06 903

(51) Int. Cl.[7] ....................... A61K 31/38; A61K 31/445; A61K 31/335; A61K 31/35
(52) U.S. Cl. ........................ 514/445; 514/315; 514/449; 514/460
(58) Field of Search .................................. 514/445, 315, 514/345, 449, 460

(56) References Cited

U.S. PATENT DOCUMENTS

| 4,371,720 | 2/1983 | Johnson et al. |
| 4,391,827 | 7/1983 | Harbert et al. |
| 5,112,820 | 5/1992 | Ward |
| 5,624,941 | 4/1997 | Barth et al. ........................... 514/326 |

FOREIGN PATENT DOCUMENTS

| 2 416 491 | 2/1974 | (DE) . |
| 0 427 518 | 6/1991 | (EP) . |
| WO 95/33429 | 12/1995 | (WO) . |
| WO 96/18600 | 6/1996 | (WO) . |

OTHER PUBLICATIONS

Database Chemical Abstracts on STN, AN 1984:563528, Moss et al, "Tetrahydrocannabinol effects on extrapyramidal motor behaviors in an animal model of Parkinson's disease", Cannabinoids: chem., Pharmacol., Ther. Aspects, [Pap. Meet] (1984), meeting Date 19, Jan. 1982.*

Database Chemical ABstracts on STN, AN 1982:28580, Moss et al., Jan. 1982.*

Database Chemical Abstracts on STN, AN 1989:433315, Lyman et al, "Delta-9 tetrahydrocannabinol: a novel treatment for experimental autoimmune encephalomyelitis", J. Neuroimmunol. (Jan. 1989), 23(1), 73–81.*

Database Chemical Abstracts on STN, AN 1991:648124, Kloog et al, "NMDA-blocking compounds, pharmaceutical compositions, their preparation and use", Eur. Pat. Appl., 16 pp. (EP 427518, May 15, 1991.*

Howlett et al., Neuropharmacology, 29: 161–165 (1990).

Matsuda et al., "Structure of a canabinoid . . . cDNA", Nature, vol. 346 (1990), pp. 561–564.

Shire et al., "An Amino-terminal Variant . . . Splicing", J.Biol.Chem., vol. 170, No. 6 (1995), pp. 3726–3731.

Galiègue et al., "Expression of central . . . subpopulations", Eur.J.Biochem., vol. 232 (1995), pp. 54–61.

Razdan, "Structure-Activity Relationships in Cannabinoids", Pharm.Revs., vol. 38, No. 2 (1986), pp. 75–149.

Huffman et al., "Recent Developments in the Medicinal Chemistry of Cannabinoids", Curr.Med.Chem., vol. 3 (1996), pp. 101–116.

Pertwee, "Cannabinoid Receptors", Academic Press (1995).

Pars et al., "Drugs Derived from Cannabinoids . . . ", J.Med.Chemistry, vol. 19, No. 4 (1976), pp. 445–453.

Razdan et al., "Drugs Derived from Cannabinoids . . . ", J.Med.Chemistry, vol. 19, No. 4 (1976), pp. 454–461.

Winn et al., "Drugs Derived from Cannabinoids . . . ", J.Med.Chemistry, vol. 19, No. 4 (1976), pp. 461–471.

Huffman et al., "Synthesis and Pharmacology . . . Receptor", J.Med.Chemistry, vol. 39 (1996), pp. 3875–3877.

Howlett et al., "Cannabinoid Receptor Agonists and Antagonists", Curr.Pharm.Design, vol. 1 (1995), pp. 343–354.

Tius et al., "Conformationally Restricted Hybrids . . . Activity", Tetrahedron, vol. 50, No. 9 (1994), pp. 2671–2680.

Tius et al., "Classical/Non-Classical Cannabinois Hybrids . . . Chain", Life Sciences, vol. 56, Nos. 23/24 (1995), pp. 2007–2012.

Mechoulam, R., Ed., "Cannabinoids as Therapeutic Agents", CRC Press (1986), pp. 121–145.

Melvin et al., "A Cannabinoid Derived Prototypical Analgesic", J.Med.Chem., vol. 27 (1984), pp. 67–71.

Melvin et al., "Structure-Activity Relationships . . . Analgesic Activity", Drug Design and Discovery, vol. 13 (1995), pp. 155–166.

(List continued on next page.)

Primary Examiner—Theodore J. Criares
(74) Attorney, Agent, or Firm—Norris McLaughlin & Marcus

(57) ABSTRACT

The present invention relates to the use of known agonists of the central cannabinoid receptor CB1 for the prophylaxis and treatment of neurodegenerative disorders, in particular for the treatment of cerebral apoplexy and craniocerebral trauma.

5 Claims, No Drawings

OTHER PUBLICATIONS

Compton et al., "Cannabinoid Structure–Activity . . . in Vivo Activities", J.Pharm. and Experimental Therapeutics, vol. 265, No. 1 (1993), pp. 218–226.

Eissenstat et al., "Aminoalkylindoles: Structure–Activity Relationships of Novel Cannabinoid Mimetics", J.Med.Chem., vol. 38 (1995), pp. 3094–3105.

D'Ambra et al., "Cattached Aminoalkylindoles: Potent Cannabinois Mimetics", Bioorganic & Medicinal Chemistry Letters, vol. 6, No. 1 (1996), pp. 17–22.

D'Ambra et al., "Conformationally Restrained Analogues . . . Cannabinoid Receptor", J.Med.Chem, vol. 35 (1992), pp. 124–135.

Bell et al., "Antinociceptive (Aminoalkyl)indoles", J.Med.Chem, vol. 34 (1991), pp. 1099–1110.

Huffman et al., "Design, Synthesis and Pharmacology of Cannabimimetic Indoles", Biorganic & Medicinal Chemistry Letters, vol. 4 (1994), pp. 563–566.

Kumar et al., "Morpholinoalkylindenes as . . . Receptor Agonists", Biorganic & Medicinal Chemistry Letters, vol. 5 (1995), pp. 381–386.

Lainton et al., "1–Alkyl–3–(1–naphthoyl)pyrroles: A New Class of Cannabinoid", Tetrahedron Letters, vol. 36, No. 9 (1995), pp. 1401–1404.

Khanolkar et al, "Head Group Analogs . . . Cannabinoid Ligand", J.Med.Chem., vol. 39 (1996), pp. 4515–4519.

Kulkarni et al., "Anandamide: An Endogenous Cannabinoid", Drugs of Today, vol. 32, No. 4 (1996), pp. 275–285.

Thomas et al., "Structure–Activity Analysis . . . Pharmacophore", J.Med.Chem., vol. 39 (1996), pp. 471–479.

Abadji et al., "(R)–Methanandamide . . . Metabolic Stability", J.Med.Chem., vol. 37 (1994), pp. 1989–1893.

Pinto et al., "Cannabinoid Receptor Binding . . . Arachidonic Acid", Molecular Pharm., vol. 46 (1994), pp. 516–522.

Mechoulam et al., "Identification of an Endogenous . . . Cannabinoid Receptors", Bio.Pharm., vol. 50, No. 1 (1995), pp. 83–90.

Hanuš et al., "Two New Unsaturated . . . Cannabinoid Receptor", J.Med.Chem., vol. 36 (1993), pp. 3032–3034.

Mechoulam et al., "Search for Endogenous Ligands of the Cannabinoid Receptor", Bio.Pharm., vol. 48, No. 8 (1994), pp. 1537–1544.

Koutek et al., "Inhibitors of Arachidonoyl Ethanolamide Hydrolysis", J.Bio.Chem., vol. 269, No. 37 (1994), pp. 22937–22940.

Felder et al., "Anandamide, an endogenous . . . signal transduction", Proc.Natl.Acad.Sci, vol. 90 (1993), pp. 7656–7660.

Edgemond et al., "The Binding of Novel Phenolic . . . Cannabinoid Receptors", Prostaglandins Leukotrienes and Essential Fatty Acids, vol. 52 (1995), pp. 83–86.

Devane et al., "Isolation and Structure of a Brain Constituent That Binds to the Cannabinoid Receptor", Science, vol. 258 (1992), pp. 1946–1949.

Adams et al., "Pharmacological and Behavioral Evaluation of Alkylated Anandamide Analogs", Life Sciences, vol. 56, Nos. 23/24 (1995), pp. 2041–2048.

Rinaldi–Carmona et al., "SR141716A, . . . cannabinoid receptor", FEBS Letters, vol. 350 (1994), pp. 240–244.

Showalter et al., "Evaluation of Binding . . . Selective Ligands", J.Pharm. E+P Ther., vol. 278, No. 3 (1996), pp. 989–999.

Seisjö, "Cell Damage in the Brain: A Speculative Synthesis", J.Cerebral Blood Flow and Metabolism, vol. 1 (1981), pp. 155–185.

Brennan, "Stroke Drugs Send Researchers Back to the Drawing Board", C&EN (1996), pp. 41–45.

Koroshetz et al., "Emerging treatments for stroke in humans",TiPS, vol. 17 (1996), pp. 227–233.

Bullock, "Pathophysiological alterations in the central nervous system due to trauma", Schweiz.med.Wschr, vol. 123 (1993), pp. 449–458 (in English with Summaries in Swedish and French).

Fischer et al., "Evolving stroke and the ischemic penumbra", Neurology, vol. 47 (1996), pp. 884–888.

* cited by examiner

USE OF KNOWN AGONISTS OF THE CENTRAL CANNABINOID RECEPTOR CB1

The present invention relates to the use of known agonists of the central cannabinoid receptor CB1 for the prophylaxis and treatment of neurodegenerative disorders, in particular for the treatment of cerebral apoplexy and craniocerebral trauma.

$\Delta^9$-Tetrahydrocannabinol ($\Delta^9$-THC) and, to a small extent, also $\Delta^8$-THC are the biologically active constituents in extracts of the plant Cannabis sativa (marihuana, hashish) and are responsible for the effects on the human central nervous system (CNS). Potential historical and contemporary therapeutic uses of cannabis preparations include, inter alia, analgesia, emesis, anorexia, glaucoma and motor disorders.

Up to now, two subtypes of cannabinoid receptors and a splice variant have been identified. The CB1 receptor (Nature 1990, 346, 561) and a splice variant CB1a (J. Biol. Chem. 1995, 270, 3726) are mainly localized in the central nervous system. The CB2 receptor was mainly found in the peripheral tissue, in particular in leucocytes, spleen and macrophages (Eur. J. Biochem. 1995, 232, 54). CB1 and CB2 receptors have seven transmembrane regions and belong to the family of G protein receptors. Both receptors are negatively coupled via $G_i/G_o$ protein to adenylate cyclase and possibly negatively coupled to the presynaptic release of glutamate [cf. J. Neurosci. 1996, 16, 4322]. CB1 receptors are moreover positively coupled to potassium channels and negatively coupled to N- and Q-type calcium channels.

It is moreover known that the cannabinoid CB1 receptor agonists are subdivided into 4 classes, the classical and nonclassical cannabinoids, the aminoalkylindoles and the icosanoids [cf. Pharmacol. Rev. 1986, 38, 75; Curr. Med. Chem. 1996, 3, 101; Cannabinoid Receptors, R. Pertwee (Ed.), Academic Press, San Diego, 1995; J. Med. Chem. 1976, 19, 445; J. Med. Chem. 1976, 19, 454; J. Med. Chem. 1976, 19, 461;WO 95/33429; DE 2416491; J. Med. Chem. 1996, 39, 3875; U.S. Pat. No. 4,371,720; Curr. Med. Chem. 1996, 3, 101; Curr. Pharm. Design 1995, 1, 343; Tetrahedr. Lett. 1994, 50 2671; Life Sci. 1995, 56, 2007; Johnson, M. R., Melvin, L. S. in "Cannabinoids as Therapeutic Agents; Mechoulam R., Ed.; CRC Press, Boca Raton Fla. 1986, pp. 121–145; J. Med. Chem. 1984, 27, 67; Pharmacol. Rev. 1986, 38, 1; Exp. Opin. Invest. Drugs 1996, 5, 1245; Pharmacol. Rev. 1986, 38, 151; Drug Design and Discovery 1995, 13, 155; J. Pharm. Exp. Ther. 1993, 265, 218; U.S. Pat. No. 4,391,827; J. Med. Chem. 1995, 38, 3094; Bioorg. Med. Chem. Lett. 6, 1996, 17; J. Med. Chem. 1992, 35, 124; J. Med. Chem. 1991, 34, 1099; Bioorg. Med. Chem. Lett. 4, 1994, 563; Bioorg. Med. Chem. Lett. 5, 1995, 381; U.S. Pat. No. 5,112,820; Tetrahedr. Lett. 1995, 1401; J. Med. Chem. 1996, 39, 4515; Drugs of Today 32, 1996, 275; J. Med. Chem. 1996, 39, 471; J. Med. Chem. 1994, 37, 1889; Mol. Pharmacol. 46, 516, 1994; Biochem. Pharmacol. 1995, 50, 83; J. Med. Chem. 1993, 36, 3032; Biochem. Pharmacol. 1994, 48, 1537; J. Biol. Chem. 1994, 269, 22937; Proc. Natl. Acad. Sci 1993, 90, 7656; J. Prostagl. Leukotr. Essen. Fatty Acids 1995, 52, 83; Science 1992, 258, 1946; Life Sci 1995, 56, 2041; FEBS Lett. 1994, 350, 240; Showalter V. M.; J. Pharmacol. Exp. Therap. 1996, 989; Pharm. Res. 13, 1996, 62; J. Med. Chem. 1997, 40, 659].

It is additionally known that cerebral apoplexy is a result of a sudden circulatory disorder of a human brain area with subsequent functional losses, with corresponding neurological and/or psychological symptoms. The causes of cerebral apoplexy can lie in cerebral haemorrhages (e.g. after a vascular tear in hypertension, arteriosclerosis and apoplectic aneurysms) and ischaemias (e.g. due to a blood pressure drop crisis or embolism). The functional losses in the brain lead to a degeneration or destruction of the brain cells (cf. Journal of Cerebral Blood Flow and Metabolism 1981, 1, 155; Chem. Eng. News 1996 (May 13), 41; Trends Pharmacol. Sci. 1996, 1, 227). Craniocerebral trauma is understood as meaning covered and open cranial injuries with involvement of the brain [cf. Schweiz. med. Wschr. 1993, 123 449].

After a cerebral vascular occlusion, only a part of the tissue volume is destroyed as a direct result of the restricted circulation and the decreased oxygen supply associated therewith [cf. Neurology 1996, 47, 884]. This tissue area designated as the infarct core can only be kept from dying off by immediate recanalization of the vascular closure, e.g. by local thrombolysis, and is therefore only limitedly accessible to therapy. The outer peripheral zone, which is as least just as large in terms of volume, also designated as the penumbra, admittedly also discontinues its function immediately after onset of the vascular occlusion, but is initially still adequately supplied with oxygen by the collateral supply and irreversibly damaged only after a few hours or even only after days. Since the cell death in this area does not occur immediately, a therapeutic opportunity reveals itself to block the unfavourable development of the course of the disease both after stroke and after trauma.

The numerous therapeutic starting points for the reduction of the infarct volume include, for example, the blocking of glutamate receptors or glutamate release, free radical scavengers, anti-inflamatory substances, substances for blocking voltage-dependent calcium or sodium channels, and GABA agonists [cf. Trends Pharmacol. Sci. 17, 1996, 227].

The inhibition of glutamatergic neurotransmission or inhibition of glutamate release can be achieved by a multiplicity of substances having differing pharmacological actions and thus differing mechanisms of action [GABA receptor ligands (Neurosci. Lett 1990, 118, 99, Br. J. Pharmacol. 1997, 120, 60), aluminium (Neurotoxicol. 1992, 13, 413), ethanol (Eur. J. Pharmacol. 1992, 219, 469), barbiturates, for example thiopental (Br. J. Pharmacol. 1996, 119, 1498), adenosine A1 receptors (Neurosci. Lett. 1996, 220, 163), $\alpha_2$-agonists (Anesthesiol. 1996, 85, 551), cannabinoid receptor agonists (J. Neurosci. 1996, 16, 4322).

For kynurenic acid (Brain Res. 1992, 592, 333) and theophylline (Brain Res 1991, 565, 353), it has been shown that these substances, although they markedly inhibit glutamate release in vitro, have no neuroprotective action in vivo.

In contrast to the speculation by Shen et al. (J. Neurosci. 1996, 16, 4322) the cannabinoid receptor agonist HU210, the (−)-enantiomer of HU-211, which is inactive on the cannabinoid receptor, is non-neuroprotective in a craniocerebral trauma model (J. Neurotrauma 1993, 10, 109).

It has now been found that the known cannabinoid CB1 receptor agonists cited above are surprisingly suitable for the prophylaxis and treatment of neurodegenerative disorders, in particular of cerebral apoplexy and craniocerebral trauma.

Preferably, [A] known agonists of the central cannabinoid receptor CB1 of the general formula (I)

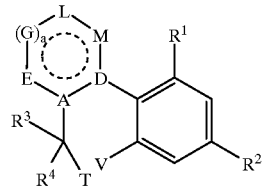

(I)

in which
A and D are identical or different and, depending on the position of a single or double bond, represent a C atom or the CH group,
E depending on the position of a single or double bond, represents the CH or $CH_2$ group or a sulphur atom,
G, L and M are identical or different and, depending on the position of a single or double bond, represent a radical of the formula $—CR^5$, $—CR^6R^7$ or $N—R^8$, in which
$R^5$, $R^6$, $R^7$ and $R^8$ are identical or different and denote hydrogen, hydroxyl, formyl, $(C_2-C_6)$-alkenyl, $(C_2-C_6)$-alkinyl, or denote $(C_1-C_6)$-alkyl which is optionally substituted by hydroxyl or $(C_1-C_4)$-alkoxy, or
$R^6$ and $R^7$ together represent a radical of the formula =O,
a represents a number 0 or 1,
$R^1$ represents hydrogen or hydroxyl, or represents $(C_1-C_{11})$-alkyl, $(C_1-C_6)$-alkoxy, $(C_1-C_6)$-alkoxycarbonyl or $(C_1-C_4)$-acyloxy, each of which is optionally substituted by hydroxyl, $(C_1-C_{10})$-alkoxy or by a group of the formula $—NR^9R^{10}$, in which
$R^9$ and $R^{10}$ are identical or different and denote hydrogen, phenyl, $(C_1-C_4)$-alkyl, or
$R^9$ and $R^{10}$, together with the nitrogen atom, form a 5- to 7-membered saturated heterocycle which can optionally additionally contain a further heteroatom of the series S and O or a radical of the formula $—NR^{11}$,
in which
$R^{11}$ denotes hydrogen, phenyl, $(C_1-C_6)$-alkyl or $(C_1-C_6)$-acyl,
$R^2$ represents $(C_1-C_{10})$-alkyl or $(C_1-C_{10})$-alkoxy, each of which is optionally substituted by phenyl, halogen, hydroxyl, azido, nitro, trifluoromethyl, trifluoromethoxy, carboxyl, $(C_1-C_4)$-alkoxy or $(C_1-C_4)$-alkoxycarbonyl or by a group of the formula $—NR^{12}R^{13}$, in which
$R^{12}$ and $R^{13}$ are identical or different and have the meanings of $R^9$ and $R^{10}$ indicated above,
$R^3$ and $R^4$ are identical or different and represent hydrogen or $(C_1-C_6)$-alkyl which is optionally substituted by hydroxyl, or
$R^3$ and $R^4$ together represent a radical of the formula $H_2C=$,
T represents $(C_1-C_6)$-alkyl or $(C_2-C_6)$-alkenyl, and V represents hydroxyl, or
T and V together with a ring closure represent an oxygen atom or a radical of the formula $—NR^4$, in which
$R^{14}$ denotes hydrogen or methyl with the exception of compounds of the following configuration

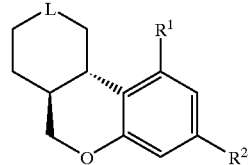

[B] non-classical cannabinoids of the general formula (Ia)

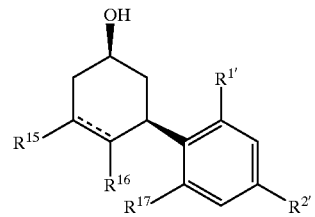

in which
$R^{1'}$ and $R^{2'}$ are identical or different and have the meanings of $R^1$ and $R^2$ indicated above,
$R^{15}$ and $R^{16}$ are identical or different and represent hydrogen or $(C_1-C_8)$-alkyl which is optionally substituted by hydroxyl, or
$R^{15}$ and $R^{16}$, together with inclusion of the C—C bond, form a phenyl ring or a 3- to 7-membered carbocyclic ring, where the ring systems are optionally substituted by $(C_1-C_6)$-alkoxycarbonyl or $(C_1-C_8)$-alkyl which for its part can be substituted by hydroxyl,
$R^{17}$ represents hydrogen, or
$R^{16}$ and $R^{17}$ together form a 6-membered saturated, partially saturated or unsaturated heterocycle which can contain a heteroatom of the series S and O or a radical of the formula $—NR^{18}$, in which
$R^{18}$ denotes hydrogen or $(C_1-C_4)$-alkyl,
and where the ring systems are optionally substituted up to 3 times identically or differently, also generally, by $(C_1-C_8)$-alkyl which for its part can be substituted by hydroxyl,

[C] the aminoalkyl indoles of the general formulae (Ib) and (Ic)

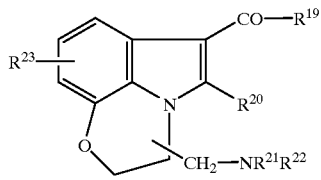

(Ib)

-continued (Ic)

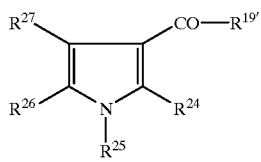

in which
- $R^{19}$ and $R^{19'}$ are identical or different and represent $(C_6-C_{10})$-aryl or a 5- to 7-membered, saturated or unsaturated heterocycle having up to 3 heteroatoms of the series S, N and/or O, each of which is optionally substituted by one or more, identical or different substituents which are selected from the group which consists of: nitro, halogen, trifluoromethyl, hydroxyl, carboxyl, or by $(C_1-C_5)$-acyl, $(C_1-C_6)$-alkoxy, $(C_1-C_6)$-alkylthio, $(C_1-C_6)$-alkoxycarbonyl and $(C_1-C_6)$-alkyl which for its part can be substituted by hydroxyl,
- $R^{20}$ represents hydrogen or methyl,
- $R^{21}$ and $R^{22}$ are identical or different and represent hydrogen or $(C_1-C_6)$-alkyl, or
- $R^{21}$ and $R^{22}$, together with the nitrogen atom, form a 5- to 7-membered, saturated or partially saturated heterocycle which can optionally contain a further oxygen or sulphur atom or a radical of the formula $-NR^{28}$, in which
  - $R^{28}$ has the meaning of $R^8$ indicated above and is identical to or different from this,
- $R^{23}$ represents hydrogen, halogen, hydroxyl, $(C_1-C_8)$-alkyl or $(C_1-C_8)$-alkoxy,
- $R^{24}$ represents hydrogen or $(C_1-C_6)$-alkyl,
- $R^{25}$ represents hydrogen, phenyl, cycloalkyl having 3 to 8 carbon atoms, or $(C_1-C_6)$-alkyl which is optionally substituted by a group of the formula $-NR^{29}R^{30}$, in which
  - $R^{29}$ and $R^{30}$ are identical or different and have the meaning of $R^9$ and $R^{10}$ indicated above,
- $R^{26}$ and $R^{27}$ represent hydrogen, or together with inclusion of the double bond form a phenyl ring,

[D] compounds of the general formula (Id)

(Id)

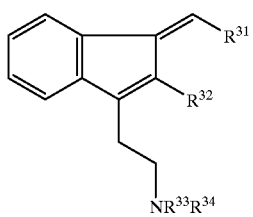

in which
- $R^{31}$ has the meaning of $R^{19}$ indicated above and is identical to or different from this,
- $R^{32}$ represents hydrogen, $(C_1-C_3)$-alkyl or $(C_1-C_3)$-alkoxy,
- $R^{33}$ and $R^{34}$ have the meaning of $R^{21}$ and $R^{22}$ indicated above and are identical to or different from this, and [E] eicosanoids of the general formula (Ie)

(Ie)

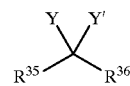

in which
- Y and Y' represent hydrogen, or
- Y and Y' together represent a radical of the formula =O or =S,
- $R^{35}$ represents $(C_{16}-C_{30})$-alkenyl having at least three double bonds,
- $R^{36}$ represents trifluoromethyl or a group of the formula $-OR^{37}$ or $-NR^{38}R^{39}$, in which
  - $R^{37}$ denotes hydrogen or $(C_1-C_{10})$-alkyl which is optionally substituted by one or more, identical or different substituents which are selected from the group which consists of: hydroxyl, halogen, trifluoromethyl, $(C_6-C_{10})$-aryl and $(C_1-C_6)$-alkoxy,
  - $R^{38}$ and $R^{39}$ have the meaning of $R^{37}$ indicated above and are identical to or different from this, or
  - $R^{38}$ and $R^{39}$, together with the nitrogen atom, form a 5- to 7-membered saturated heterocycle which can optionally contain a further heteroatom of the series S and O or a group of the formula $-NR^{40}$, in which
    - $R^{40}$ has the meaning of $R^8$ indicated above and is identical to or different from this, and their salts and isomeric forms,
are used in the control of neurodegenerative disorders, in particular cerebral apoplexy and craniocerebral trauma.

The compounds used according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid. Very particularly preferred salts are those mentioned above which are formed by the amine function.

Physiologically acceptable salts can also be metal or ammonium salts of the compounds according to the invention. Particularly preferred salts are, for example, sodium, potassium, magnesium or calcium salts, as well as ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

In the context of the present invention, the substituents in general have the following meaning:

$(C_1-C_{11})$-, $(C_1-C_{10})$-, $(C_1-C_8)$-, $(C_1-C_6)$-, $(C_1-C_4)$- and $(C_1-C_3)$-alkyl in general represent, depending on the above-mentioned substituents, a straight-chain or branched hydrocarbon radical having 1 to 11 carbon atoms. Examples which may be mentioned are methyl, ethyl, propyl, isopropyl, butyl, isobutyl, pentyl, isopentyl, hexyl, isohexyl, heptyl, isoheptyl, octyl and isooctyl.

($C_{16}$–$C_{30}$)- and ($C_2$–$C_6$)-alkenyl in general represent, depending on the abovementioned substituents, a straight-chain or branched hydrocarbon radical having 2 to 30 carbon atoms and one or more, preferably having one, two or at least 3 double bonds. Examples which may be mentioned are allyl, propenyl, isopropenyl, butenyl, isobutenyl, pentenyl, isopentenyl, hexenyl, isohexenyl, heptenyl, isoheptenyl, octenyl and isooctenyl.

($C_2$–$C_6$)-Alkinyl in general represents a straight-chain or branched hydrocarbon radical having 2 to 6 carbon atoms and one or more, preferably having one or two triple bonds. The lower alkyl radical having 2 to approximately 5 carbon atoms and a triple bond is preferred. An alkenyl radical having 2 to 4 carbon atoms and a triple bond is particularly preferred. Examples which may be mentioned are acetylene, 2-butine, 2-pentine and 2-hexine.

Cycloalkyl in general represents a cyclic hydrocarbon radical having 3 to 8 carbon atoms. The cyclopropane, cyclopentane and the cyclohexane rings are preferred. Examples which may be mentioned are cyclopentyl, cyclohexyl, cycloheptyl and cyclooctyl.

Aryl in general represents an aromatic radical having 6 to 10 carbon atoms. Preferred aryl radicals are phenyl and naphthyl.

($C_1$–$C_{10}$)-, ($C_1$–$C_6$)- and ($C_1$–$C_4$)-alkoxy in general represent, depending on the abovementioned substituents, a straight-chain or branched hydrocarbon radical bonded via an oxygen atom and having 1 to 10 carbon atoms. Examples which may be mentioned are methoxy, ethoxy, propoxy, isopropoxy, butoxy, isobutoxy, pentoxy, isopentoxy, hexoxy, isohexoxy, heptoxy, isoheptoxy octoxy or isooctoxy.

($C_1$—$C_6$)- and ($C_1$–$C_5$)-acyl in general represent straight-chain or branched lower alkyl having 1 to 6 carbon atoms which are bonded via a carbonyl group. Examples which may be mentioned are: acetyl, ethylcarbonyl, propylcarbonyl, isopropylcarbonyl, butylcarbonyl and isobutylcarbonyl.

($C_1$–$C_6$)- and ($C_1$–$C_4$)-alkoxycarbonyl can be represented, for example, by the formula

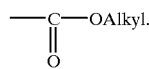

Alkyl in this connection represents a straight-chain or branched hydrocarbon radical having 1 to 6 or 1 to 4 carbon atoms. Examples which may be mentioned are the following alkoxycarbonyl radicals: methoxycarbonyl, ethoxycarbonyl, propoxycarbonyl, isopropoxycarbonyl, butoxycarbonyl or isobutoxycarbonyl.

Halogen in the context of the invention represents fluorine, chlorine, bromine and iodine.

($C_1$–$C_6$)-Alkylthio in general represents a straight-chain or branched hydrocarbon radical bonded via a sulphur atom and having 1 to 6 carbon atoms. Examples which may be mentioned are methylthio, ethylthio and propylthio.

($C_1$–$C_4$)-Acyloxy can be represented, for example, by the formula

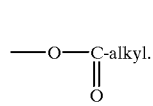

Alkyl in this connection represents a straight-chain or branched hydrocarbon radical having 1 to 4 carbon atoms. Examples which may be mentioned are the following acyloxy radicals: methcarbonyloxy, ethylcarbonyloxy and propylcarbonyloxy.

Saturated, partially saturated and unsaturated heterocycle in the context of the present invention in general represents a 5- to 7-membered, preferably 5- to 6-membered, heterocycle which can contain up to 3 heteroatoms of the series S, N and/or O. Examples which may be mentioned are: pyridyl, thienyl, furyl, pyrrolyl, pyrrolidinyl, piperazinyl, pyrimidyl, thiazolyl, oxazolyl, imidazolyl, morpholinyl or piperidyl.

The compounds according to the invention can exist in stereoisomeric forms which either behave as image and mirror image (enantiomers), or which do not behave as image and mirror image (diastereomers). The invention relates both to the enantiomers or diastereomers and to their respective mixtures. These mixtures of the enantiomers and diastereomers can be separated in a known manner into the stereoisomerically uniform constituents.

Preferably used compounds according to the invention are those of the general formula (I), in which in the compounds of the general formula (I)
A, D, E, G, a, L, M, T and V have the meaning indicated above,
$R^1$ represents hydroxyl or the radical of the formula —O—CO—$CH_3$ or —O—CO—($CH_3$)—N($C_2H_5$)$_2$,
$R^3$ and $R^4$ together represent the =$CH_2$ radical, or
$R^3$ and $R^4$ represent hydrogen, methyl or the ($CH_2$)$_3$—OH radical,
in which in the compounds of the general formula (Ia),
$R^2$ and $R^{17}$ have the meaning indicated above,
$R^{1'}$ represents hydroxyl,
$R^{15}$ and $R^{16}$ represent hydrogen, or together with the inclusion of the C—C bond form a pyridyl or CH—OH— substituted phenyl ring,
in which in the compounds of the general formula (Ib)
$R^{19}$ represents naphthyl,
$R^{20}$ represents methyl,
$R^{23}$ represents hydrogen, and
$R^{21}$ and $R^2$, together with the nitrogen atom, form a morpholine ring,
in which in the compounds of the general formula (Ic)
$R^{19'}$ represents methoxy-substituted naphthyl,
$R^{24}$ represents hydrogen,
$R^{25}$ represents phenyl, ($C_1$–$C_6$)-alkyl or the radical 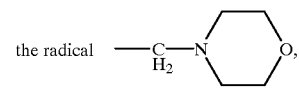

$R^{26}$ and $R^{27}$ represent hydrogen or phenyl,
in which in the compounds of the general formula (Id)
$R^{31}$ represents napthyl which is optionally substituted by methoxy, $R^{32}$ represents hydrogen or methyl, $R^{33}$ and $R^{34}$, together with the nitrogen atom, represents morpholine, in which in the compounds of the general formula (Ie)

Y and Y' represent hydrogen or together represent the =O radical, $R^{35}$ represents $(C_{16}-C_{21})$-alkenyl, and $R^{36}$ represents trifluoromethyl or the radical of the formula $-NR^{38}R^{39}$, in which $R^{38}$ and $R^{39}$ are identical or different and denote hydrogen or $(C_1-C_3)$-alkyl which is optionally substituted by fluorine or hydroxyl, and their salts and isomeric forms, in the control of neurodegenerative disorders, in particular cerebral apoplexy and craniocerebral trauma.

The following compounds:

(1)
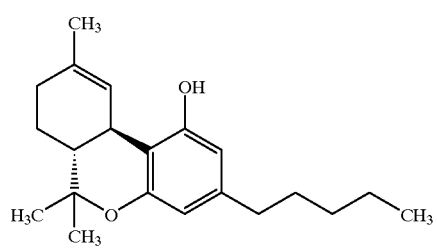

(2)
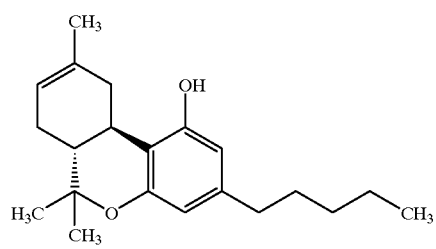

(3)
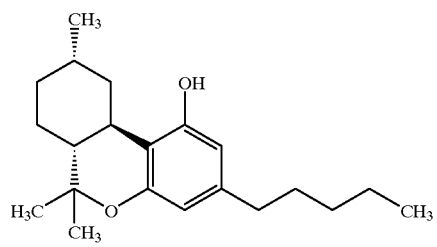

(4)
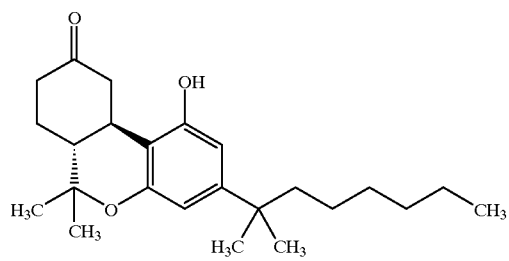

-continued (5)
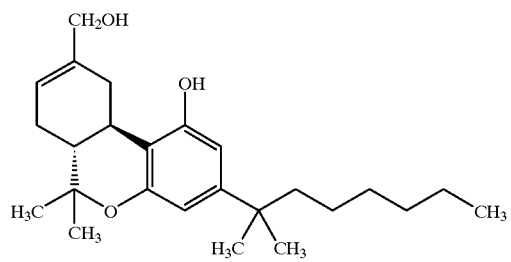

(6)
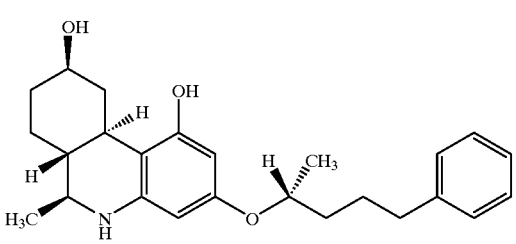

(7)
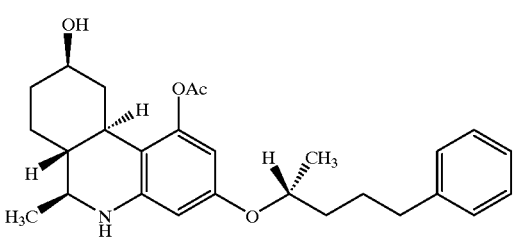

(8)
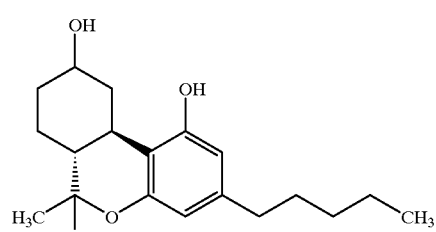

(9)
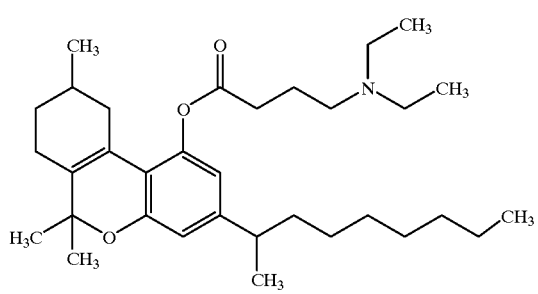

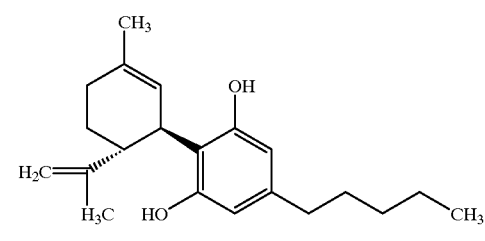
(10)
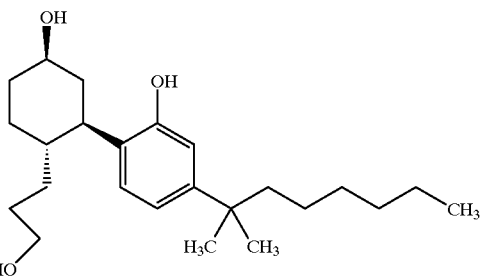
(15)
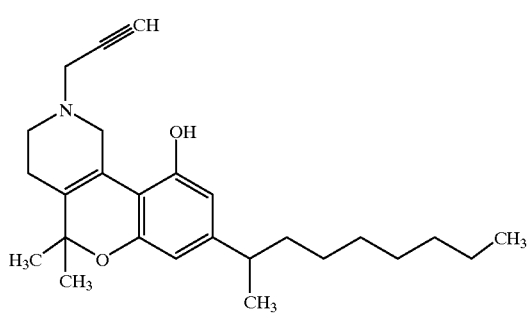
(11)
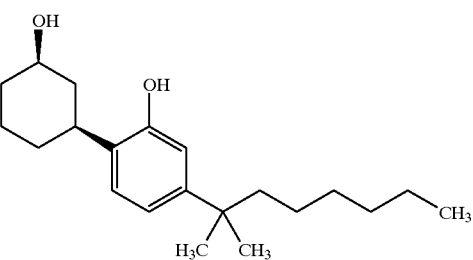
(16)
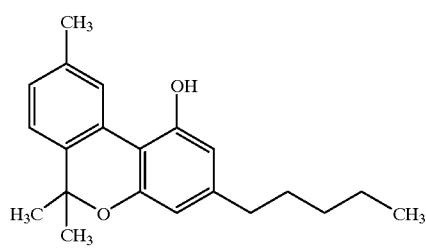
(12)
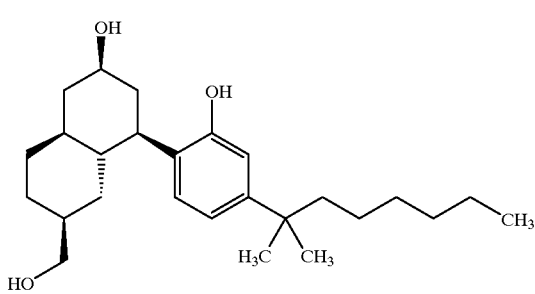
(17)
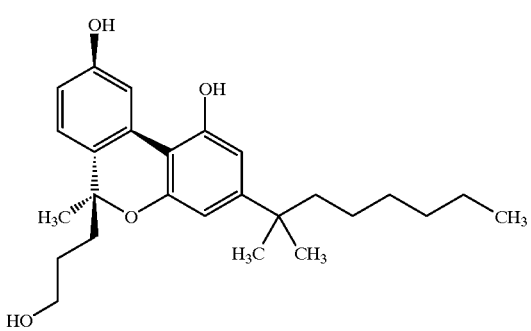
(13)
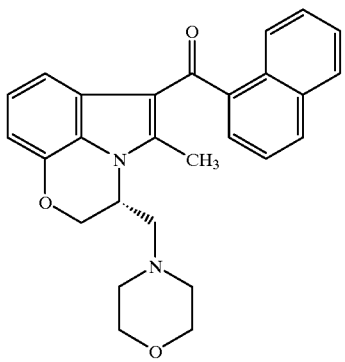
(18)
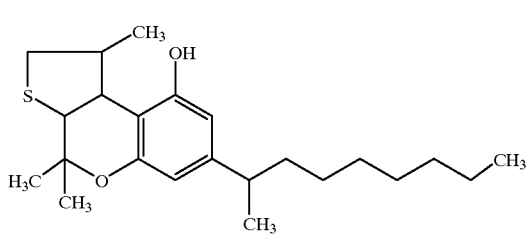
(14)
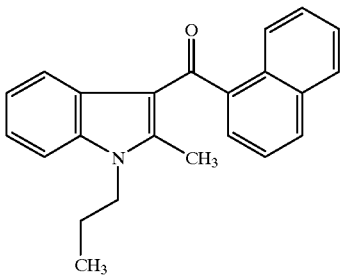
(19)

-continued
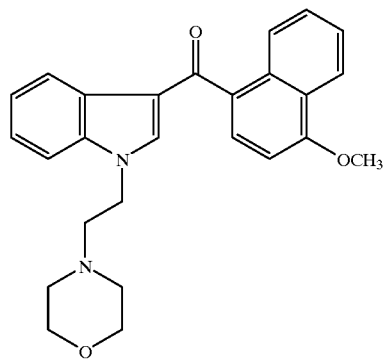
(20)
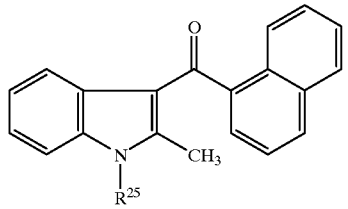
R²⁵ = nButyl (21)
R²⁵ = Phenyl (22)
R²⁵ = nHexyl (23)
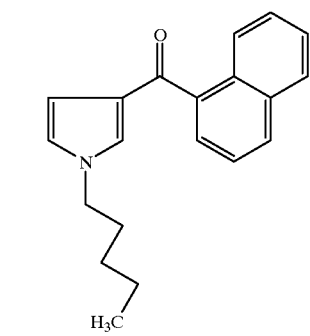
(24)
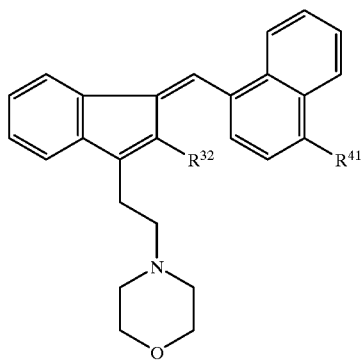
R³² = H; R⁴¹ = H (25)
R³² = CH₃; R⁴¹ = H (26)
R³² = H; R⁴¹ = OCH₃ (27)
R³² = CH₃ R⁴¹ = OCH₃ (28)
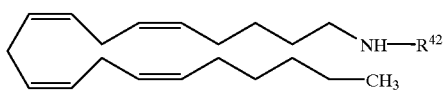
R⁴² = H (29)
R⁴² = CH₃ (30)
-continued
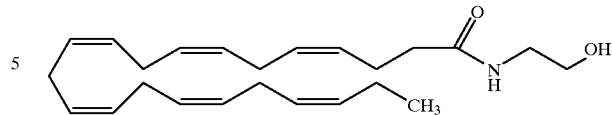
(31)
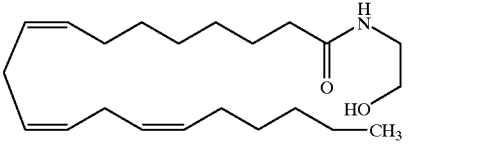
(32)
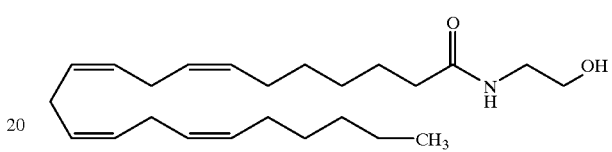
(33)
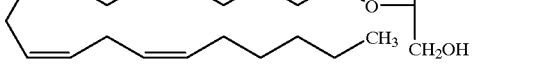
(34)
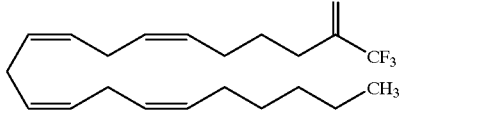
(35)
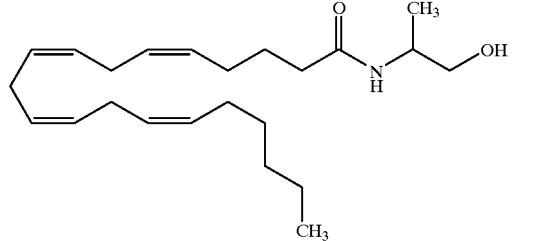
(36)
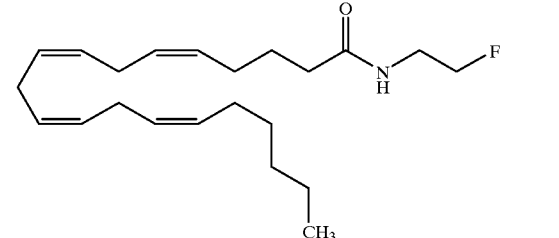
(37)
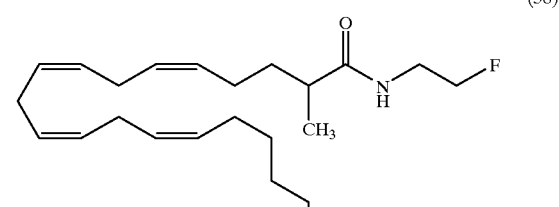
(38)

are very particularly preferably used for the prophylaxis and treatment of neurodegenerative disorders, in particular for the treatment of cerebral apoplexy and craniocerebral trauma.

The abovementioned known compounds can be prepared by customary methods [cf. the abovementioned references].

Cannabinoid receptor CB-1 agonists in the sense of the invention are compounds which in the CB-1 luciferase reporter gene test described below have an $IC_{50}$ value of less than $10^{-5}$ M.

CB1 Luciferase Reporter Gene Test

1. Cloning of the Rats Cannabinoid Receptor CB1

Total RNA from rat brain (the tissue was taken from freshly killed animals and shock-frozen in liquid nitrogen) was isolated by means of acidic guanidinium thiocyanate/phenol/chloroform extraction (J. Biol. Chem. 1979, 18, 5294) and converted into cDNA by means of reverse transcriptase and random primers (in each case from Invitrogen). The polymerase chain reaction (PCR, conditions: 4 min at 94° C., 1×; 1 min at 94° C.; 2 min at 53° C.; 1 min at 72° C., 50 cycles; 1 min at 94° C., 2 min at 53° C., 4 min at 72° C., 1×) was carried out in a Perkin Elmer thermocycler using the enzyme Taq polymerase (Perkin Elmer); the oligonucleotide primers employed (bases 99 to 122: 5'→3', "down"; 1556–1575: 3'→5', "up") were derived from the published sequence of the rat cannabinoid receptor (Nature 1990, 346, 561) and were synthesized on a DNA synthesizer, model 1380 from Applied Biosystems. One part of the PCR reaction was separated in a 1% strength agarose gel in 1×TBE buffer and then stained with ethidium bromide, only one band having the expected length being visible (approximately 1.5 kb). This PCR product was subcloned in the TA cloning vector (Invitrogen) and the nucleotide sequence of the insert was determined with T7 DNA polymerase (Sequenase, USA/Amersham) by the dideoxynucleotide chain termination reaction. The insert has a length of 1477 base pairs and contains an open reading frame of 1419 base pairs which corresponds to a protein of 473 amino acids. The number of base pairs, the position of the open reading frame and the number of amino acids agree with the published sequence. Computer analyses were carried out with the aid of the GCG software suite (Genetic Computer Group). The cDNA insert was subcloned in the expression vector pRc/CMV (Invitrogen) after partial digestion with HindIII and NotI (Biolabs). This construct (plasmid CMV-RH) was employed for transfection experiments.

2. Stable Transfection of the CHOluc9 Reporter Cells

CHOluc9 cells were cultured in 50% Dulbecco's modified Eagle Medium/50% F-12 (DMEM/F12) which contained 10% foetal calf serum (FCS). Transfections were prepared in 6-well plates. 7.5 μg of Qiagen-purified CMV-RH plasmid DNA were added per $10^5$ cells with the DOTAP transfections system, corresponding to the experimental protocol of the manufacturer (Boehringer Mannheim). Transfected cells were selected with 1 mg/ml G418 and individual clones were obtained by limiting dilution on 96-well plates. Cell lines which express the cannabinoid receptor were identified in the presence of forskolin for the inhibition of reporter gene expression after incubation with the cannabinoid receptor agonist, WIN-55,2121-2. Several stably transfected and subcloned cell lines were further characterized by means of RT-PCR, as described under 1.

3. Test Optimization and Pharmacological Characterization of the CHOCB1 Reporter Cell Line With the aim of high sensitivity and reproducibility, low variance and good suitability for carrying out on the robotic system, the luciferase test was optimized by variation of several test parameters, such as, for example, cell density, duration of the growth phase and the test incubation, forskolin concentration, medium composition. The following test protocol was used for pharmacological characterization of the cells and for robot-assisted substance screening: the stock cultures were cultured in 50% Dulbecco's modified Eagle Medium/50% F-12 (DMEM/F12) with 10% FCS at 37° C. under 10% $CO_2$ and in each case split 1:10 after 2 to 3 days. Test cultures were inoculated into 96-well plates at 5000 cells per well and cultured at 37° C. for 70 hours. The cultures were then carefully washed with phosphate-buffered saline and reconstituted using serum-free Ultra-CHO medium (Bio-Whittaer). The substances dissolved in DMSO were diluted 1×in medium and pipetted into the test cultures (maximum DMSO final concentration in the test mixture: 0.5%). 20 minutes later, forskolin was added and the cultures were then incubated at 37° C. in an incubator for 3 hours. The supernatants were then removed and the cells were lysed by addition of 25 μl of lysis reagent (25 mM triphosphate, pH 7.8 with 2 mM DTT, 10% glycerol, 3% TritonX100).

Directly after this, luciferase substrate solution (2.5 mM ATP, 0.5 mM luciferin, 0.1 mM coenzyme A, 10 mM tricine, 1.35 mM $MgSO_4$, 15 mM DTT, pH 7.8) was added, the mixture was briefly shaken, and the luciferase activity was measured using a Hamamatzu camera system.

For inactivation of $G_i$ proteins, the test cultures were treated with 5 ng/ml (final conc.) of pertussis toxin for 16 hours before the test.

The $IC_{50}$ values were calculated using the Graph Pad Prism program (Hill equation, specific: one-site competition).

| Example | CB1 luciferase reporter gene test $IC_{50}$ [nM] |
| --- | --- |
| 1 | 13.32 |
| 5 | 0.48 |
| 15 | 0.23 |
| 18 | 1.55 |

Binding Studies on Rat Cortex Membranes

Membrane protein is prepared from different tissues or from cells by standard methods. Buffer, labelled ligands, DMSO or test substance are pipetted together, then 100 μg of protein are added, and the mixture is well mixed and incubated in a water bath at 30° C. for 60 min. After expiry of the incubation time, the reaction is stopped by addition of ice-cold incubation buffer to each tube. After filtering off, washing is carried out with ¾ ml of incubation buffer. The filters are transferred to minivials and the radioactivity is determined in a liquid scintillation counter.

| Example | Binding to rat cortex membranes $K_i$ [nM] |
| --- | --- |
| 1 | 1.69 |
| 5 | 1.00 |
| 15 | n.t. |
| 18 | 0.06 |

Inhibition of Glutamate Release

After decapitation of a rat, the skull is opened, and the brain is lifted out and cut through along the median fissure. The hippocampus is exposed, separated from the remaining tissue, cut into 350 µm thick sections and incubated at 37° C. in straining vessels for 60 min. Followed by basal value and stimulation 1 with 75 mM KCl (S1), the sections are incubated with test substance and then the stimulation with KCl and test substance (S2) is repeated. The glutamate concentration of the samples to be investigated is then measured by means of an enzymatic reaction (GLDH) and fluorometric measurement of NADH. By means of a calibration curve, the glutamate content of the sample is determined, and with knowledge of the protein content the glutamate content/mg of protein can be calculated. The ratio S2/S1 is compared; glutamate release inhibitors reduce this ratio in a concentration-dependent manner.

| Example No. | Inhibition of glutamate release % Inhibition @ 1 µM |
| --- | --- |
| 1 | no effect |
| 5 | 20 |
| 15 | |
| 18 | 50 |

Hypothermia

1. Agonism Testing

Five minutes after determination of the basal body temperature via an oesophageal temperature probe, the test substance is administered (i.v.). A control group receives only the solvent for the test substances, likewise i.v. The body temperature is measured 7.5, 15, 30 and 60 minutes after i.v. administration. The group size per dose is 5–7 animals (rats).

| Example No. | Hypothermia $ED_{-1° C.}$[a] [mg/kg i.v.] |
| --- | --- |
| 1 | 0.8 |
| 5 | 0.01 |
| 15 | 0.03 |
| 18 | 0.2 |

[a]Necessary dose in order to achieve a maximum temperature drop of 1° C.

2. Antagonism Testing

The specific CB1 antagonist SR 141716A or, to the control group, only the solvent (Solutol/0.9% NaCl) is administered intraperitoneally 60 minutes before administration of test substance. The basal body temperature is measured five minutes before administration of SR 141716A via oesophageal temperature probe. The further procedure corresponds to the method "agonism testing". The group size per dose is 5–7 animals (rats).

Permanent Focal Cerebral Ischaemia in the Rat (MCA-O)

Under isoflurane anaesthesia, the median cerebral artery is exposed on one side and the latter and its side branches are irreversibly sealed by means of electrocoagulation. As a result of the intervention a cerebral infarct is formed. During the operation, the body temperature of the animal is kept at 37° C. After wound closure and wearing off of the anaesthesia, the animals are again released into their cage. The administration of substances is carried out according to different time schemes and via different administration routes (i.v., i.p.) after occlusion. The infarct size is determined after 7 days. To do this, the brain is removed, worked up histologically and the infarct volume is determined with the aid of a computer-assisted analysis system.

| Example No. | % reduction in the infarct volume | Dose[a] |
| --- | --- | --- |
| 1 | 31 | 1.0 mg/kg |
| 5 | 48 | 0.01 mg/kg |
| 18 | 20 | 0.03 mg/kg |

[a]The substance administration as intravenous bolus injections in each case directly, 2 and 4 h after occlusion.

Subdural Haematoma in the Rat (SDH)

Under the anaesthesia, the animals' own blood is injected subdurally on one side. An infarct is formed under the haematoma. Substance administration is carried out according to different time schemes and via different administration routes (i.v., i.p.). The infaract size is determined as described in the model of permanent focal ischaemia in the rat (MCA-O).

| Example No. | % reduction in the infarct volume | Dose[a] |
| --- | --- | --- |
| 1 | 50% | 0.3 mg/kg |
| 5 | 58% | 0.001 mg/kg |

[a]The substance administration as intravenous bolus injections in each case directly, 2 and 4 h after trauma.

The present invention also includes pharmaceutical preparations which besides inert, non-toxic, pharmaceutically suitable auxiliaries and excipients contain one or more compounds of the general formulae (I)–(Ie) or which consist of one or more active compounds of the formulae (I)–(Ie), and processes for the production of these The active compounds of the formulae (I)–(Ie) should be present in these preparations in a concentration of 0.1 to 99.5% by weight, preferably of 0.5 to 95% by weight of the total mixture.

Besides the active compounds of the formulae (I)–(Ie), the pharmaceutical preparations can also contain other pharmaceutical active compounds.

The abovementioned pharmaceutical preparations can be prepared in a customary manner by known methods, for example using the auxiliary(ies) or excipient(s).

In general, it has proved advantageous to administer the active compound(s) of the formulae (I)–(Ie) in total amounts of approximately 0.01 to approximately 100 mg/kg, preferably in total amounts of approximately 1 mg/kg to 50 mg/kg, of body weight every 24 hours, if appropriate in the form of several individual doses, to achieve the desired result.

However, if appropriate it may be advantageous to deviate from the amounts mentioned, mainly depending on the nature and on the body weight of the subject treated, on the individual behaviour towards the medicament, the nature and severity of the disorder, the type of preparation and administration, and the time at or interval after which administration takes place.

What is claimed is:

1. A method of preventing or treating a condition in a patient, said condition being selected from cerebral apoplexy, craniocerebral trauma, and a combination of cerebral apoplexy and craniocerebral trauma, and said method comprising administering to said patient an amount of an agonist of the cannabinoid receptor CB1 which is effective to prevent or treat said condition, wherein said agonist has the formula (I):

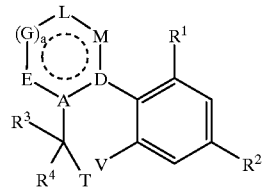

(I)

in which

A and D are identical or different and represent, depending on the position of a single or double bond, a C atom or the CH group;

E represents, depending on the position of a single or double bond, the CH group, the $CH_2$ group or a sulfur atom;

G, L and M are identical or different and represent, depending on the position of a single or double bond, a radical of the formula $-CR^5$, $-CR^6R^7$ or $-NR^8$; in which $R^5$, $R^6$, $R^7$ and $R^8$ are identical or different and represent hydrogen, hydroxyl, formyl, $C_{2-6}$-alkenyl, $C_{2-6}$-alkinyl or $C_{1-6}$-alkyl, which alkyl is optionally substituted by hydroxyl or $C_{1-4}$-alkoxy; or $R^6$ and $R^7$ together represent a radical of the formula =O;

a represents a number 0 or 1;

$R^1$ represents hydrogen or hydroxyl; or represents $C_{1-11}$-alkyl, $C_{1-6}$-alkoxy, $C_{1-6}$-alkoxycarbonyl or $C_{1-4}$-acyloxy, each of which is optionally substituted by hydroxyl, $C_{1-10}$-alkoxy or by a group of the formula $-NR^9R^{10}$; in which $R^9$ and $P^{10}$ are identical or different and represent hydrogen, phenyl or $C_{1-4}$-alkyl; or $R^9$ and $R^{10}$, together with the nitrogen atom to which they are bonded, form a 5- to 7-membered saturated heterocyclic ring which in addition to the nitrogen atom optionally contains in the heterocyclic ring a sulfur atom, an oxygen atom or a radical of the formula $-NR^{11}$; in which $R^{11}$ represents hydrogen, phenyl, $C_{1-4}$-alkyl or $C_{1-6}$-acyl;

$R^2$ represents $C_{1-10}$-alkyl or $C_{1-10}$-alkoxy, each of which is optionally substituted by phenyl, halogen, hydroxyl, azido, nitro, trifluoromethyl, trifluoromethoxy, carboxyl, $C_{1-4}$-alkoxy, $C_{1-4}$-alkoxycarbonyl or a group of the formula $-NR^{12}R^{13}$; in which $R^{12}$ and $R^{13}$ are identical or different and represent hydrogen, phenyl or $C_{1-4}$-alkyl; or $R^{12}$ and $R^{13}$, together with the nitrogen atom to which they are bonded, form a 5- to 7-membered heterocyclic ring which in addition to the nitrogen atom optionally contains in the heterocyclic ring a sulfur atom, an oxygen atom or a radical of the formula $-NR^{11}$; in which $R^{11}$ has the meaning indicated above;

$R^3$ and $R^4$ are identical or different and represent hydrogen or $C_{1-6}$-alkyl, which alkyl is optionally substituted by hydroxyl; or $R^3$ and $R^4$ together represent a radical of the formula $H_2C=$;

T represents $C_{1-6}$-alkyl or $C_{2-6}$-alkenyl; and

V represents hydroxyl; or

T and V together with a ring closure represent an oxygen atom or a radical of the formula $-NR^{14}$; in which $R^{14}$ represents hydrogen or methyl;

or a salt or stercoisometeric from thereof;

with the exception of any compound of the following configuration:

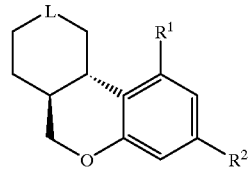

wherein L, $R^1$ and $R^2$ have the meanings indicated above.

2. A method of preventing or treating a condition in a patient, said condition being selected from cerebral apoplexy, craniocerebral trauma and a combination of cerebral apoplexy and craniocerebral trauma, and said method comprising administering to said patient an amount of an agonist of the cannabinoid receptor CB1 which is effective to prevent or treat said condition, wherein said agonist has the formula (Ia):

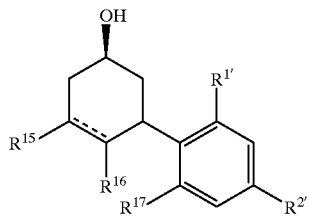

(Ia)

in which $R^{1'}$ represents hydrogen or hydroxyl; or represents $C_{1-11}$-alkyl, $C_{1-6}$-alkoxy, $C_{1-6}$-alkoxycarbonyl or $C_{1-4}$-acyloxy, each of which is optionally substituted by hydroxy, $C_{1-10}$-alkoxy or by a group of the formula $-NR^9R^{10}$; in which R⁹ and R¹⁰ are identical or different and represent hydrogen, phenyl or C₁₋₄-alkyl; or R⁹ and R¹⁰, together with the nitrogen atom to which they are bonded, form a 5- to 7-membered saturated heterocyclic ring which in addition to the nitrogen atom optionally contains in the heterocyclic ring a sulfur atom, an oxygen atom or a radical of the formula —NR¹¹; in which R¹¹ represents hydrogen, phenyl, C₁₋₆-allkyl or C₁₋₆-acyl;

R²′ represents C₁₋₁₀-alkyl or C₁₋₁₀-alkoxy, each of which is optionally substituted by phenyl, halogen, hydroxyl, azido, nitro, trifluoromethyl, trifluoromethoxy, carboxyl, C₁₋₄-alkoxy, C₁₋₄-alkoxycarbonyl or a group of the formula —NR¹²R¹³; in which R¹² and R¹³ are identical or different and represent hydrogen, phenyl or C₁₋₄-alkyl; or R¹² and R¹³ together with the nitrogen atom to which they are bonded, form a 5- to 7-membered saturated heterocyclic ring which in addition to the nitrogen atom optionally contains in the heterocyclic ring a sulfur atom, an oxygen atom or a radical of the formula —NR¹¹; in which R¹¹ has the meaning indicated above;

R¹⁵ and R¹⁶ are identical or different and represent hydrogen or C₁₋₈-alkyl, which alkyl is optionally substituted by hydroxyl; or R¹⁵ and R¹⁶ together with the C—C bond to which they are bonded form a phenyl ring or a 3- to 7-membered carbocyclic ring, which phenyl ring and 3- to 7-membered carbocyclic ring are optionally substituted by C₁₋₆-alkoxycarbonyl or C₁₋₈-alkyl, where the C₁₋₈-alkyl is, in turn, optionally substituted by hydroxyl;

R¹⁷ represents hydrogen; or

R¹⁶ and R¹⁷ together with a ring closure from a 6-membered saturated, partially saturated or unsaturated heterocyclic ring which contains a sulfur atom, an oxygen atom or a group of the formula —NR¹⁸; in which R¹⁸ represents hydrogen or C₁₋₄-alkyl;

where the 6-membered saturated partially saturated or unsaturated heterocyclic ring is optionally substituted, optionally generally, 1 to 3 times by identical or different C₁₋₈-alkyl groups, where the C₁₋₈-alkyl groups are, in turn, optionally substituted by hydroxyl, or a salt or stereoisomeric form thereof.

3. The method according, to claim 2, in which the agonist of the cannabinoid receptor CB1 is selected from the group consisting, of:

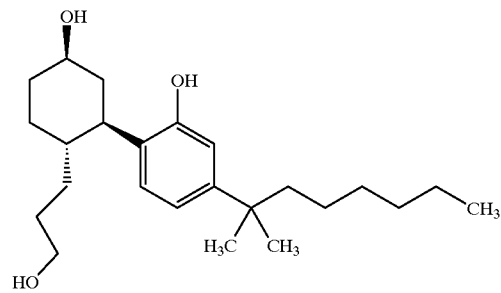
(15)

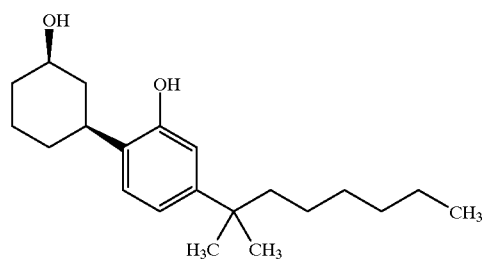
(16)

and

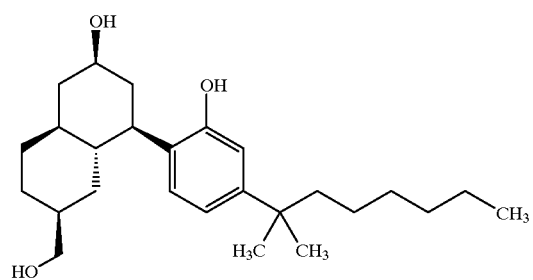
(17)

or a salt or stereoisomeric form thereof.

4. The method according to claim 1, in which the agonist of the cannabinoid receptor CB1 is selected from the group consisting of

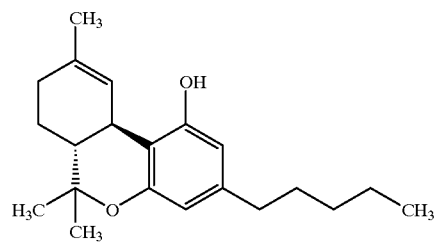
(1)

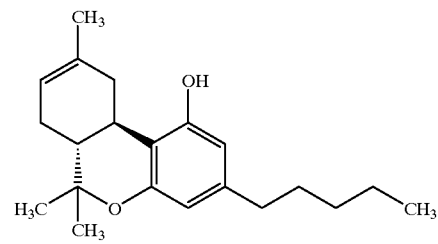
(2)

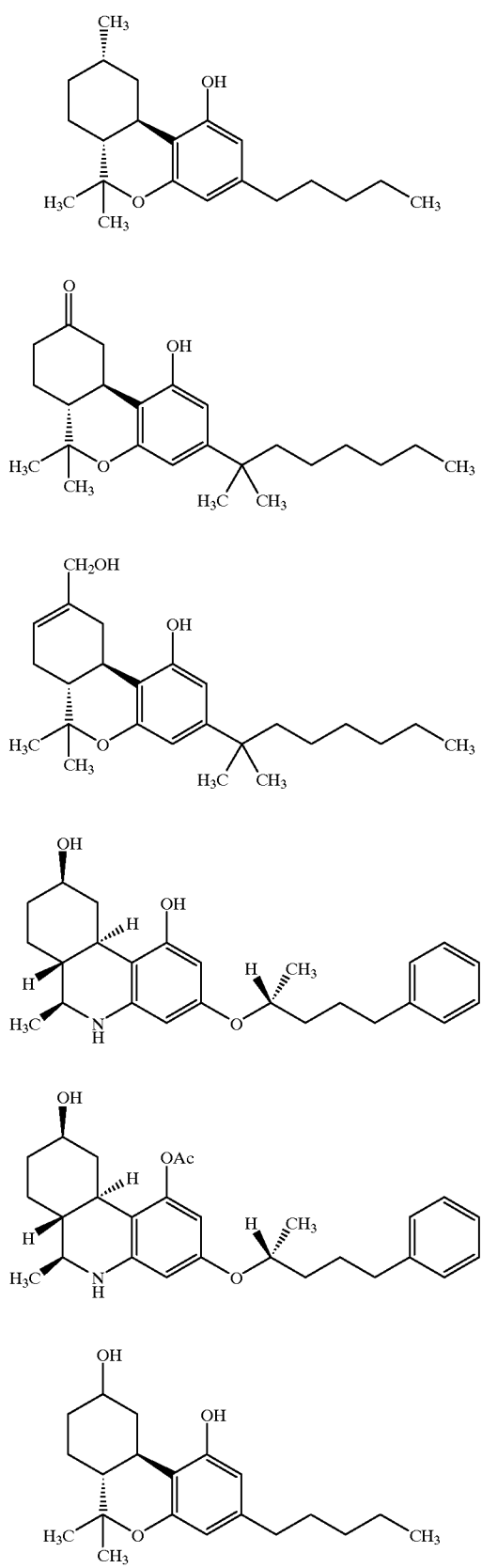
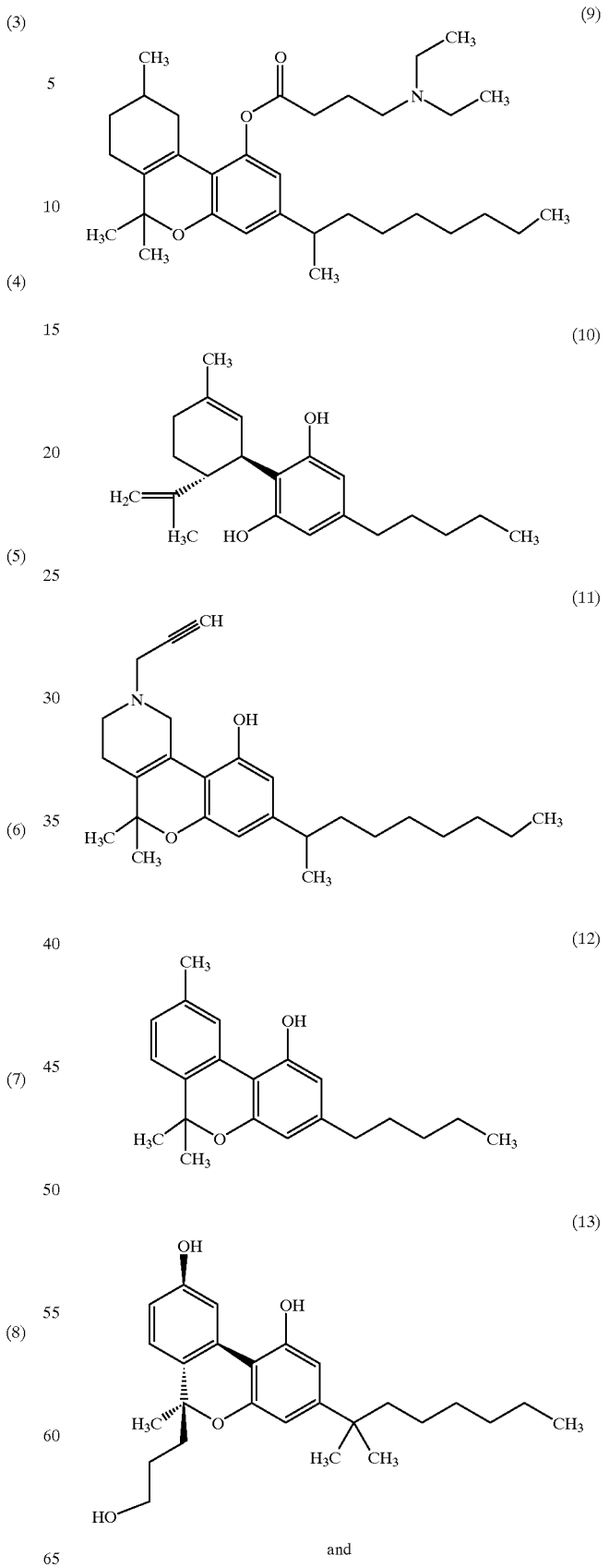

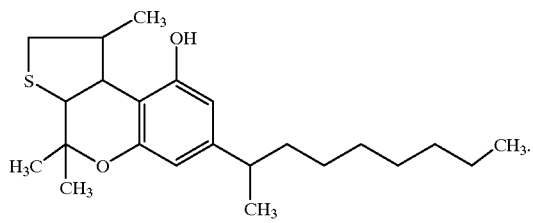
(14)
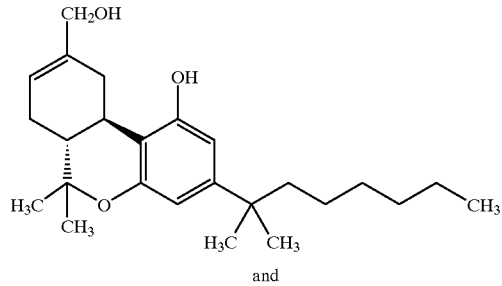
(5)
and
5. The method according to claim 4, in which the agonist of the cannabinoid receptor CB1 is selected the group consisting of
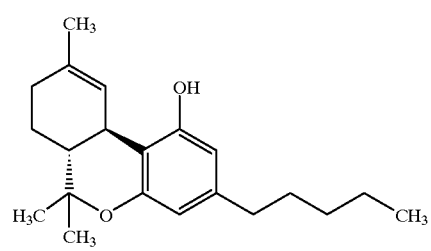
(1)
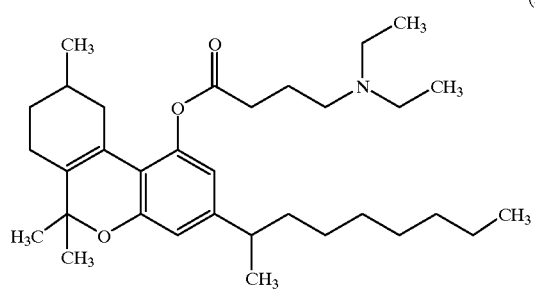
(9)
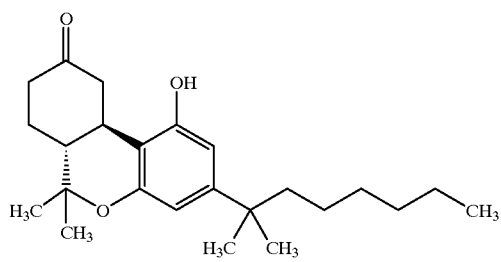
(4)
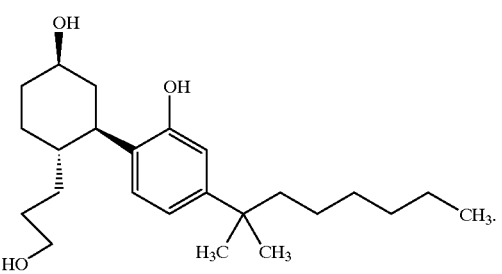
(15)
* * * * *

UNITED STATES PATENT AND TRADEMARK OFFICE
CERTIFICATE OF CORRECTION

PATENT NO.   : 6,284,788 B1
DATED        : September 4, 2001
INVENTOR(S)  : Joachim Mittendorf et al.

It is certified that error appears in the above-identified patent and that said Letters Patent is hereby corrected as shown below:

<u>Column 21,</u>
Line 56, change "generally" to -- geminally --

Signed and Sealed this

Eighteenth Day of February, 2003

JAMES E. ROGAN
*Director of the United States Patent and Trademark Office*